US012370033B2

(12) United States Patent
Darlington

(10) Patent No.: US 12,370,033 B2
(45) Date of Patent: Jul. 29, 2025

(54) METHOD FOR DETERMINING THE PREGNANCY STATE OF AN ANIMAL

(71) Applicant: AGSCENT PTY LTD, Carwoola (AU)

(72) Inventor: Bronwyn Darlington, Carwoola (AU)

(73) Assignee: Agscent Pty Ltd, Carwoola (AU)

( * ) Notice: Subject to any disclaimer, the term of this patent is extended or adjusted under 35 U.S.C. 154(b) by 165 days.

(21) Appl. No.: 17/926,552

(22) PCT Filed: May 20, 2021

(86) PCT No.: PCT/AU2021/050481
§ 371 (c)(1),
(2) Date: Nov. 18, 2022

(87) PCT Pub. No.: WO2021/232110
PCT Pub. Date: Nov. 25, 2021

(65) Prior Publication Data
US 2023/0200964 A1 Jun. 29, 2023

(30) Foreign Application Priority Data
May 20, 2020 (AU) .................................. 2020901611

(51) Int. Cl.
*A61D 17/00* (2006.01)
*G01N 30/72* (2006.01)
*G01N 33/497* (2006.01)
*G01N 30/02* (2006.01)

(52) U.S. Cl.
CPC ....... *A61D 17/006* (2013.01); *G01N 30/7206* (2013.01); *G01N 33/497* (2013.01); *G01N 2030/025* (2013.01)

(58) Field of Classification Search
CPC .. A61D 17/006; G01N 30/72; G01N 30/7206; G01N 33/497; G01N 33/4977
See application file for complete search history.

(56) References Cited

U.S. PATENT DOCUMENTS

| 6,416,479 | B1 * | 7/2002 | Seidman | A61B 5/0836 |
| | | | | 600/529 |
| 10,172,698 | B2 * | 1/2019 | Carton | G16H 40/67 |
| 11,181,519 | B2 * | 11/2021 | Haick | A61B 5/7264 |

OTHER PUBLICATIONS

Gabrieli et al., Innovative method for early detection followed by chemical characterisation of pregnancy in grazing beef cows, 2019, Precision Livestock Farming '19 downloaded from https://library.wur.nl/WebQuery/wurpubs/fulltext/541504#page=740 on Sep. 29, 2024. (Year: 2019).*
International Searching Authority, International Search Report, PCT Application No. PCT/AU2021/050481 dated Jul. 26, 2021, AU.
International Searching Authority, Written Opinion of the International Searching Authority, PCT Application No. PCT/AU2021/050481 dated Jul. 26, 2021, AU.

(Continued)

*Primary Examiner* — Erika J. Villaluna
(74) *Attorney, Agent, or Firm* — Reichel Stohry Dean LLP; Natalie J. Dean

(57) ABSTRACT

Disclosed herein is a method for determining a pregnancy state of an animal. The method comprises detecting an amount of one or more biomarkers in a breath sample from the animal, the amount of the or each biomarker being indicative of a pregnancy state of the animal.

9 Claims, 14 Drawing Sheets

(56) References Cited

OTHER PUBLICATIONS

Nakhlel et al., Artificially Intelligent Nanoarray for the Detection of Preeclampsia under Real-World Clinical Conditions, Advanced Materials Technologies 1(9): 1600132 (2016), doi.org/10.1002/admit.201600132, Wiley Online Library, US.

Borras et al., Exhaled breath condensate methods adapted from human studies using longitudinal metabolomics for predicting early health alterations in dolphins, Analytical and Bioanalytical Chemistry 409(28): 6523-6536 (2017), doi.org/10.1007/s00216-017-0581-6, Springer Science+Business Media, DE.

Klein et al., Detection of pregnancy in horses by breath analysis using differential ion mobility spectrometry (DMS), European Respiratory Journal 38: 1201 (2011), European Respiratory Society, CH.

Bikov et al., Exhaled breath volatile alterations in pregnancy assessed wit electronic nose, Biomarkers 16(5): 476-484 (2011), doi.org/10.3109/1354750X.2011.598562, Taylor & Francis, UK.

Breath test detects cattle pregnancies, Farming Ahead 334: 55 (Nov. 2019), available at https://pir.sa.gov/au/_data/assets/pdf_file/0011/369461/Cattle_yard_designs_-_Case_studies_from_Farming_Ahead_November_2019.pdf, Kondinin Group, AU.

Townsend, New device to sniff out livestock pregnancies, The Land (Jul. 11, 2019), available at https://www.theland.com.au/story/6261581/new-device-to-sniff-out-livestock-pregnancies/, Australian Community Media, AU.

Manzoli et al., Volatile compounds monitoring as indicative of female cattle fertile period using electronic nose, Sensors & Actuators B: Chemical 282: 609-616 (2019), Elsevier, Inc., NL.

Barman et al., Gas chromatographic-mass spectrometric analysis of chemical volatiles in buffalo (*Bubalus bubalis*) urine, Theriogenology 80: 654-658 (2013), Elsevier Inc., NL.

International Searching Authority, International Preliminary Report on Patentability, PCT Application No. PCT/AU2021/050481 dated Aug. 26, 2022, AU.

Klein et al., Breath analysis using Ion Mobility Spectrometry (IMS) as diagnostic tool in equine reproduction medicine, Biomedical Tech 58 (Supp. 1) (2013), doi:10.1515/bmt-2013-4449, KeAi Publishing, CN.

* cited by examiner

METHOD FOR DETERMINING THE PREGNANCY STATE OF AN ANIMAL

PRIORITY

This application is related to, claims the priority benefit of, and is a 35 U.S.C. 371 national stage application of International Patent Application No. PCT/AU2021/050481, filed May 20, 2021, which is related to and claims the priority benefit of Australian Patent Application No. 2020901611, filed May 20, 2020. The contents of the aforementioned applications are hereby incorporated by reference in their entireties into this disclosure.

TECHNICAL FIELD

The present invention relates to methods for determining the pregnancy state of an animal.

BACKGROUND ART

Determining the pregnancy state of animals is desirable for many reasons. In the case of livestock, for example, a knowledge of the pregnancy state of individual animals in a herd, flock, etc. enables for more accurate planning and better farm management. For example, the economic burden of maintaining non-pregnant animals in the same manner as pregnant animals is significant. Thus, by identifying the pregnancy state of an animal (e.g. a cow) as early as possible, non-pregnant animals can be separated from pregnant animals and fed/treated more appropriately (and cheaply). Further, identifying non-pregnant animals as soon as possible enables them to be culled (e.g. if infertile) or put back in with a bull, ram, etc. to hopefully become impregnated.

A number of techniques are currently available for detecting the pregnancy state of animals, including for livestock such as cows. Currently, pregnancy testing for cows is most commonly performed by rectal palpation. Palpation is generally conducted at a minimum of 42 days post insemination, and is an invasive and physically demanding procedure that is usually conducted by an experienced veterinarian or animal handler.

Portable ultrasonic pregnancy detectors may instead be used to detect pregnancy in cows and other animals. However, whilst such detectors can provide a high accuracy of pregnancy status (and other information such as the age of the foetus), the method is also invasive, and is slower and more expensive than rectal palpation.

Knowledge of an animal's pregnancy state is a key factor for making better business decisions on farm and could result in significantly improved economic outcomes. It would therefore be advantageous to provide alternative methods for determining the pregnancy state of an animal. It would be especially advantageous if at least some of such alternative methods did not require invasive procedures, specialised personnel (e.g. veterinarians) or equipment (e.g. ultrasounds), or were capable of detecting pregnancy earlier than is currently possible.

SUMMARY OF INVENTION

The inventor of the invention the subject of the present application has discovered that the breath of female bovines (generally referred to as cows) contains biomarkers which are characteristic of pregnancy. As will be described in further detail below, the inventor has been able to demonstrate that a non-invasive breath sampling method (which only takes a few seconds) can be used to determine the pregnancy state of a cow. Given the inventor's identification of these biomarkers (and subsequent characterisation of some of these biomarkers) and their understanding of the reasons for these biomarkers being present in the cow's breath, they believe that it is reasonable to expect that their discovery will be generally applicable to other species of animals, and especially other livestock animals such as sheep and pigs.

In a first aspect therefore, the present invention provides a method for determining a pregnancy state of an animal. The method comprises detecting an amount of one or more biomarkers in a breath sample from the animal, the amount of the or each biomarker being indicative of a pregnancy state of the animal.

The identification of a biomarker or biomarkers in an animal's breath, which can be collected using a simple device such as that disclosed in the applicant's co-pending international (PCT) patent application no. PCT/AU2020/050318 (WO 2020/198790), and which is/are indicative of the pregnancy state of the animal is a discovery of significant economic benefit. Breath samples may, for example, be taken from animals at a convenient time or at convenient intervals post insemination (either artificially or by a bull), with cows identified as being pregnant immediately separated from the herd for appropriate management. The inventor's preliminary data indicates that the animal's pregnancy state may be determined using the method of the present invention as early as 16 days post-conception, which would be a reduction from the earliest current scan of ultrasound being 28 days and a significant reduction from common practice being post-40 days (oftentimes post 80 days) using current techniques. Furthermore, given its inherently non-invasive nature, breath sampling can be carried out on-farm without the need for specialist veterinary expertise.

In some embodiments, the method may comprise comparing the detected amounts of the one or more biomarkers to a predetermined biomarker profile. The predetermined biomarker profile may, for example, comprise an accumulation of detected amounts of the one or more biomarkers in breath samples from the same species of animal having a categorised pregnancy state. Thus, and as will be described in further detail below, data regarding the presence and amount of the relevant biomarker(s) in the animal's breath can be compared to a biomarker profile of a non-pregnant (i.e. empty or dry) animal.

In some embodiments, detecting an amount of the one or more biomarkers may comprise chromatographically resolving the breath sample. The breath sample may, for example, be chromatographically resolved by gas chromatography. The breath sample may, for example, be chromatographically resolved by gas chromatography in combination with other techniques such as mass spectroscopy (i.e. GC-MS), where mass spectra for a plurality of points of the chromatographically resolved breath sample may be produced. In such embodiments, the mass spectral dataset produced may be analysed to determine the pregnancy state of the animal.

In some embodiments, the mass spectral dataset may be analysed using a multivariate analysis such as partial least squared discriminant analysis (PLS-DA, described in further detail below).

In some embodiments, detecting an amount of the one or more biomarkers may comprise contacting the breath sample with a plurality of sensors that are configured to sense the one or more biomarkers, whereby a cumulative response of the sensors is indicative of the animal being pregnant. As will be described below, "Electric Nose" sensors that are configurable to quickly perform on-site analysis of gasses are commercially available and the inventor has demonstrated that one such sensor was able to be used to detect pregnancy in cows. The inventor expects that "Electric Nose" sensors will be adaptable for the detection of biomarkers indicative of a cow's pregnancy state, and that no more than routine trial and experimentation will be required to adapt such sensors for the biomarkers determined to be indicative of pregnancy in other animals. As would be appreciated, a portable breath screening device which detects pregnancy in a non-invasive, accurate and economically viable fashion would likely be of great interest to veterinarians, dairy farmers, primary producers and graziers.

In some embodiments, at least one of the one or more biomarkers may be a metabolite of a metabolic process affected by the pregnancy state of the animal. In such embodiments, an amount of the at least one biomarker in the breath sample may increase because it is (they are) a metabolite of a metabolic process that is upregulated in pregnant animals. In such embodiments, an amount of the at least one biomarker in the breath sample may decrease because it is (they are) a metabolite of a metabolic process that is downregulated in pregnant animals.

In some embodiments, the biomarker may be selected from one or more of the following: toluene, hexanal, tridecane, tetradecane, propanoic acid, pentane,1,3-epoxy-4-methyl, 3,5 dimethyl 2-octanone, 4-undecanone and 4-octanone.

In some of such embodiments, the amounts of hexanal, tridecane, tetradecane, propanoic acid, pentane,1,3-epoxy-4-methyl, 3,5 dimethyl 2-octanone, 4-undecanone and 4-octanone may increase in the breath sample of a pregnant animal. In some of such embodiments, the amount of toluene may decrease in the breath sample of a pregnant animal.

In a second aspect, the present invention provides a method for determining a pregnancy state of an animal. The method comprises detecting an amount of one or more biomarkers indicative of a pregnancy state of the animal in a breath sample from the animal, and analysing the detected amount of the one or more biomarkers to determine the pregnancy state of the animal.

In a third aspect, the present invention provides a method for determining a pregnancy state of an animal. The method comprises detecting an amount of one or more biomarkers indicative of a pregnancy state of the animal in a breath sample from the animal, and comparing the detected amount of the one or more biomarkers to a predetermined biomarker profile to determine the pregnancy state of the animal.

In a fourth aspect, the present invention provides a sensor for detecting a pregnancy state of an animal. The sensor comprises a detector for detecting an amount of one or more biomarkers indicative of a pregnancy state of an animal in a breath sample from the animal, and an analyser for analysing the detected amount of the one or more biomarkers to determine the pregnancy state of the animal.

In some embodiments of the fourth aspect, the sensor may comprise a plurality of sensors that are configured to detect the presence (or not) of one or more of the biomarkers, whereby a predetermined cumulative response of the plurality of sensors is indicative of the animal being pregnant.

In some embodiments of the fourth aspect, the sensor may be used in the methods of the first, second and third aspects of the present invention.

Other aspects, features and advantages of the present invention will be described below.

BRIEF DESCRIPTION OF THE DRAWINGS

Embodiments of the present invention will be described in further detail below with reference to the following drawings, in which.

DETAILED DESCRIPTION OF THE INVENTION

Figure 1:
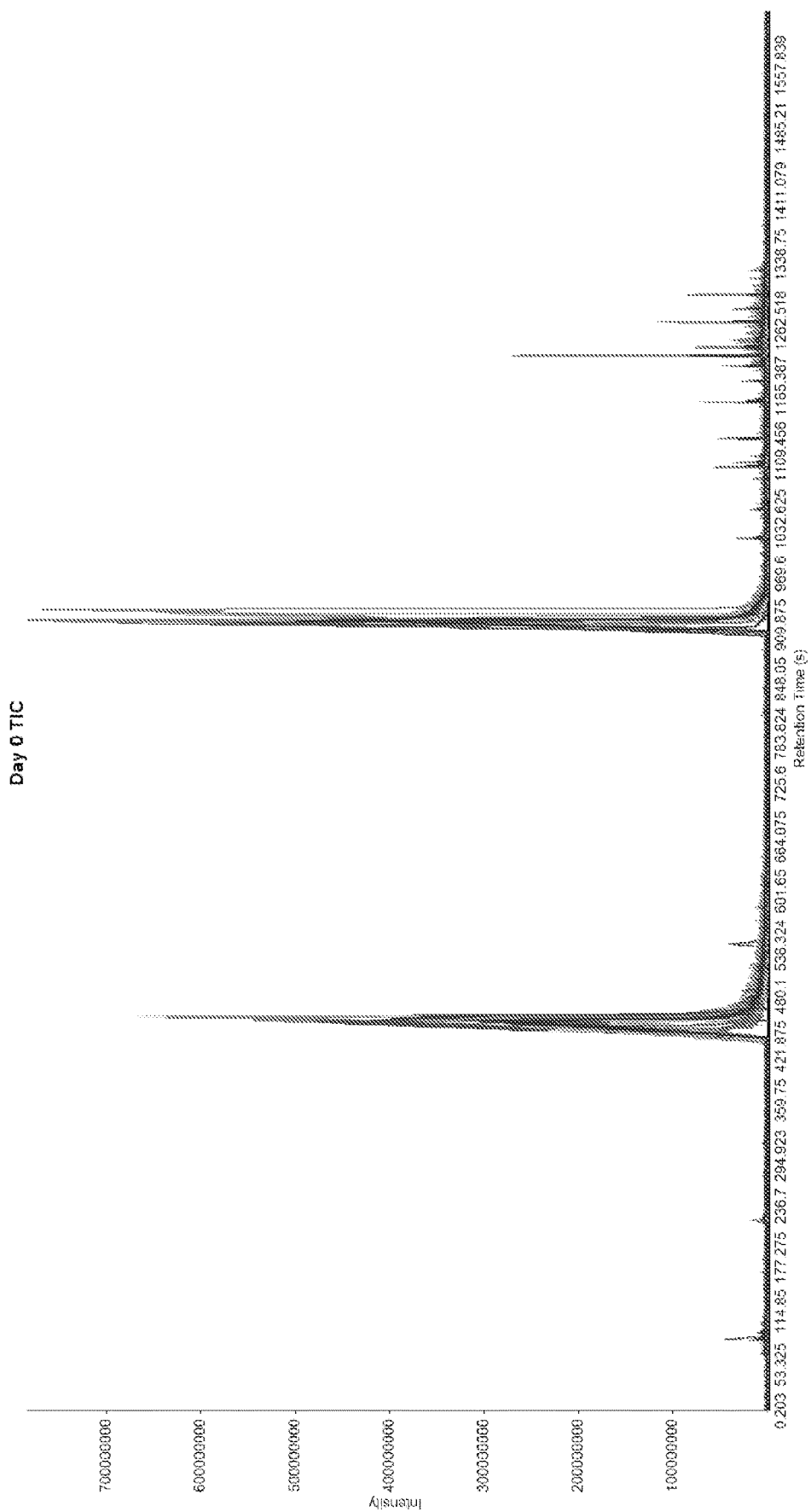
FIG. 1 is a total ion chromatograph (TIC) of breath samples taken on day 0 and used in establishing a baseline for determining cow pregnancy.

The overarching purpose of the present invention is to determine the pregnancy state of an animal using methods that either do not require invasive procedures, veterinarians or specialised equipment, or which are capable of detecting pregnancy at a relatively early stage.

In one aspect, the present invention therefore provides a method for determining a pregnancy state of an animal. The method comprises detecting an amount of one or more biomarkers in a breath sample from the animal, the amount of the or each biomarker being indicative of a pregnancy state of the animal.

As noted above and as will be described in further detail below, the inventor has discovered that the breath of cows contains biomarkers in the form of volatile organic compounds which are characteristic of pregnancy. The amounts of these biomarkers change when the cow is pregnant, with these changes being correlatable with the cow's pregnancy state. The inventor postulates that the changes in the amounts of the biomarkers that they have discovered to be related to the cow's pregnancy state may be due to changes such as metabolic changes, physical changes or hormonal changes which occur in the cow's bodies when they are pregnant.

For example, without wishing to be bound by theory, and noting that many metabolic pathways would likely change upon animals becoming pregnant, the inventor notes that the metabolic pathways associated with the production of vitamin A from 13-Carotene significantly increase in pregnant cows, and that some of the biomarkers they have discovered are conceivably metabolites of that metabolic process. (3-Carotene is a precursor to vitamin A, which is an important vitamin for the healthy growth of a foetus. (3-Carotene is ingested when an animal eats certain plant materials and can safely be stored in the animal's body (in contrast to vitamin A, which is toxic in large quantities) until such time as the animal's body needs vitamin A. When vitamin A is required (e.g. by a developing foetus), the stored (3-Carotene is enzymatically converted into vitamin A, and the inventor speculates that the at least some of the biomarkers described herein may be metabolites of this process.

Other biomarkers may be the result of other systemic changes that occur when the animal is pregnant, such as those associated with placenta formation, embryo growth and development and/or the cessation of the estruses cycle.

Given this rationale for the presence of these biomarkers in the cow's breath, the inventor believes that it is reasonable to expect that this discovery will be generally applicable to other breeds and species of animals, and especially to other livestock animals such as sheep and pigs. Even if the metabolic pathways described above are not, in fact, responsible for the biomarkers which the inventor has discovered in cows' breath and which can be used to characterise the cow's pregnancy state, other species of animals would be expected to experience metabolic changes not dissimilar to those of cows upon becoming pregnant, and techniques similar to those described below could be performed in order to identify relevant biomarker(s) and to determine the amount(s) of the biomarker(s) in the animal's breath that are indicative of the animal's pregnancy state. As will be appreciated, different biomarkers may be relevant for different species of animal (or even different breeds of the same animal) and the inventor's preliminary data indicates that the biomarker profile may change during pregnancy. However, it is believed that the techniques described herein can be utilised by a person skilled in the art to identify relevant biomarkers, and hence any given animal's pregnancy state, without undue burden or the need for further experimentation.

Biomarkers identified in the breath samples of cows and characterised using the NIST Mass Spectrometry Data Center include toluene, hexanal, tridecane, tetradecane, propanoic acid, pentane,1,3-epoxy-4-methyl, 3,5 dimethyl 2-octanone, 4-undecanone and 4-octanone. The inventor notes that, of these biomarkers, the amount of hexanal, tridecane, tetradecane, propanoic acid, pentane,1,3-epoxy-4-methyl, 3,5 dimethyl 2-octanone, 4-undecanone and 4-octanone increases in the breath sample of a pregnant animal, and that the amount of toluene decreases in the breath sample of a pregnant animal.

Hexanal is an alkyl aldehyde which has been identified in cows during the estrus period in cervicovaginal mucus. Cervicovaginal mucus is constituted with mucins, ions, salts, and water and it is assumed that this mucus emits an important volatile signal indicative of the reproductive state of the cow.

Tridecane is a straight chain alkane that has been found at estrus and diestrus stages in Indian antelope. An upregulation of tridecane has also been identified in rats from clitoral gland in estrus.

Propanoic acid is a short-chain saturated fatty acid which has been found to be involved in reproduction and to take part in the development and metabolic programming process of embryos. Other studies have observed a 3-fold increase in propionic acid in cows at the late stage of estrus, with propionic acid being found in bovine faeces specifically at the estrus. Propanoic acid is also an inhibitor of prostaglandin synthesis and it has been found in rats that propanoic acid increase progesterone secretion. Such an action of increasing progesterone and decreasing prostaglandin is a prerequisite of pregnancy established in the female animals.

Pentane,1,3-epoxy-4-methyl is an epoxy ketone, which are versatile building blocks in the synthesis of natural products and biologically active compounds. It has been observed that epoxy ketones are significantly increased in day 18 of estrus cycle and highly utilized at the early stages of pregnancy. Epoxy ketones also reportedly play an important role for prostaglandins synthesis, and an increase in epoxy ketones at early pregnancy might be due to the synthesis of prostaglandins to induce interferon-tau for changing the environment in the endometrium of uterus for establishing pregnancy.

3,5 dimethyl 2 octanone has been detected in wild animal urine samples as a volatile compound and is significantly present in beef heifer cervicovaginal mucus during ovulation and estrus period. 4 undecanone has also been detected in heifer cervicovaginal mucus during late estrus.

4 octanone has also been found to be present in beef heifer cervicovaginal mucus during late estrus. Octanone was also detected in the female dog that was in estrus, as well as in urine sample of Murrah buffalo, in pre-estrus, estrus and post-estrus stages.

As noted above, the inventor postulates that these biomarkers (or at least some of these biomarkers) may be metabolites of one or more metabolic processes in the animal. An increase in the amount of the biomarker(s) in the breath sample may be because it is a metabolite of a metabolic process that is upregulated in pregnant animals. Similarly, a decrease in the amount of the biomarker(s) in the breath sample may be because it is a metabolite of a metabolic process that is downregulated in pregnant animals. An increase in the amount of one or more of the biomarkers in combination with a decrease in the amount of other of the biomarkers may, for example, be indicative of the pregnancy state of the animal. Alternatively (or in addition), at least some of these biomarkers may be produced in the animal as part of the animal's response to becoming pregnant (e.g. placental formation and changes in its estruses cycle).

Again, techniques similar to those described herein could be performed in order to identify a biomarker or combination of biomarkers (the same as or different to those listed above) in the breath of an animal other than a cow which are indicative of that animal's pregnancy state. It is envisaged that such biomarkers could be identified without undue burden or experimentation in light of the teachings contained herein, even should it not be possible to associate those biomarkers with a particular metabolic pathway or combination of pathways.

Thus, the inventor believes that the disclosure contained herein is sufficient to enable a person skilled in the art to extrapolate the teachings contained herein (relating to breath samples from cows) to other animals. The inventor notes that, even if their current understanding of the reasons for the changes in the amounts of the biomarkers described herein is not correct, that the experimental data and methodology described herein could still be adapted to empirically determine effective biomarker profiles for other animals.

The method of the present invention may comprise the step of comparing the detected amounts of the one or more biomarkers to a predetermined biomarker profile. The predetermined biomarker profile may be specific to a particular species of animal, or even specific to a particular breed of animal, if differences in the biomarkers and the amounts of the biomarkers are found to exist. In effect, the predetermined biomarker profile provides a baseline against which the relative increase or decrease in the amounts of the biomarkers in the animal's breath can be assessed in determining the animal's pregnancy state.

The predetermined biomarker profile may be obtained in any suitable manner. Typically, the predetermined biomarker profile would comprise (or be defined by) a data set including an accumulation of detected amounts of the one or more biomarkers in breath samples from the same species of animal, and which have a known pregnancy state (even if this condition is applied to the data after its sampling and subsequent analysis). For example, tens, hundreds or even thousands of animals' breath samples may be analysed to determine their biomarker content and changes post-conception, with the results of those analyses being combined with the animals' respective pregnancy states (possibly using subsequently obtained data) to provide the predetermined biomarker profile. A specific predetermined biomarker profile for cows, and the method used to create this profile, will be described in further detail below.

Any suitable technique may be used to detect the amounts of the biomarkers in the animal's breath sample. Given that one of the intended applications of the present invention is for pregnancy testing of livestock, techniques that use portable equipment, which is preferably robust, simple to operate and reliable, would be preferred. However, equipment that utilises such point of use analytical methods are typically secondary in nature, i.e. they need to be calibrated against a known analytical reference method of high precision and accuracy.

In this regard, the standard method of gas sample analysis is gas chromatography-mass spectrometry (GCMS), used around the world in analytical laboratories for medical, forensic and many other industrial applications. GCMS combines the separating capabilities of gas chromatography with the molecular identification power of mass spectrometry. Whilst this equipment is generally not portable, requires skilled operators, is expensive and requires significant maintenance, it may be used to validate a selection of results in order to establish or maintain a calibration of a simpler detection device, such as an "Electric nose" sensor of the kind described below. Furthermore, some emerging technologies utilise GC-MS and may provide a new generation of analytical tools that are far smaller than conventional GC-MS instruments. Such technology, if developed, may allow for GC-MS techniques to be practical for use "in-field".

GCMS outputs two separate but highly linked data outputs; a chromatogram, which is a multivariate fingerprint of the samples as measured by the GC system as total intensity vs. time.

A single chromatogram is generated per sample measured and the patterns in the chromatogram were anticipated to be indicative of pregnant/non-pregnant cows when assessed using multivariate pattern recognition algorithms. A mass spectrum is generated for every point measured in the chromatogram and the length of the mass spectrum is determined by the highest molecular weight compound detected in the sample. In general, the mass spectrum is usually interpreted when a peak in the chromatogram is determined to be important and its chemical identification is to be established.

In some embodiments therefore, detecting an amount of the one or more biomarkers may comprise chromatographically resolving the breath sample (e.g. by gas chromatography or analytical techniques involving GC such as GC-MS). Whilst GC equipment would generally not be portable and might not be appropriate for all applications of the present invention, it would be very useful in establishing and maintaining the predetermined biomarker profile, as well as for calibrating and maintaining more portable electronic devices (e.g. sensors such as the "Electric nose" sensors described below). The inventor also notes that there may be occasions when the accuracy and reliability of GC systems make them commercially viable (e.g. for larger farms).

Once collected, the detected amount(s) of the biomarker(s) in the breath sample would usually need to be analysed before an indication of the animal's pregnancy state can be provided. Any suitable data analysis methodology that is compatible with the detection techniques described herein may be used in the present invention.

For example, as noted above the dataset generated mas spectra produced for a plurality of points of a sample that has been resolved by gas chromatography is complex and would usually require the use of multivariate analysis (MVA) techniques. MVA techniques are well suited to the analysis of highly multidimensional data and have previously been used in the agriculture, pharmaceutical and petrochemical industries for real time predictions and early event detection, as well as in major processing industries for the extraction and interpretation of complex patterns in data that cannot be analysed by simple statistical routines.

Three particular methods of analysis are expected to be useful for the evaluation of data obtained in accordance with the present invention, namely principal component analysis (PCA), Partial Lest Squared Discriminant Analysis (PLS-DA) and Partial Least Squares Regression (PLSR). Examples of these methods of analysis being used in the context of the present invention will be described below. These are standard and well documented methods, known as multivariate methods as they assess more than one variable at a time.

PCA is a method of analysis which provides a highly visual environment for detecting patterns in complex data, such as the total ion chromatographs (TICs) generated by GC-MS. It allows an analyst to see if there are any within group variations (e.g. pregnant vs. non-pregnant animals) and any time dependent changes in the groups. The main advantage of PCA is that it is highly interpretable and can be validated.

PLS DA is an alternative method to PCA that provides more direct modelling capabilities when the classes of data (e.g. data from a particular sampling time, such as Day 0, Day 14, etc.) are known. Time of sampling (e.g. day) can then be used as a class to discriminate between any changes on a day.

PLSR is a multivariate regression method that allows for the development of a predictive model utilising multiple inputs from a sensor. In the context of the present invention (and as described below), the changes in biomarkers in the GC-MS data may be calibrated against the responses generated by the "Electronic nose". Like PCA, PLSR is also highly visual, is interpretable and can be validated, which can provide much more reliability and integrity to the prediction results generated by multivariate models compared to other methods of analysis. PLSR also has inbuilt diagnostics to ensure that prediction results are valid.

In other embodiments, an amount of the one or more biomarkers may be detected using a sensor, preferably a portable sensor and even more preferably a hand-held sensor coupled to a sampling device such as that disclosed in the applicant's co-pending international (PCT) patent application no. PCT/AU2020/050318 (WO 2020/198790). In such embodiments, detecting an amount of the one or more biomarkers may comprise contacting the breath sample with a plurality of sensors that are configured to sense the presence of the biomarker(s), whereby a (predetermined) cumulative response of the sensors is indicative of the animal being pregnant. Such sensors will be described in further detail below.

The breath sample may be collected from the animal using any suitable technique. In order to reduce the risk of contamination (e.g. by food or saliva), the breath sample may, for example, be collected from the animal's nose.

In practice, breath samples may be taken from the animals at any suitable interval or at the convenience of the primary producer. Given the significantly higher costs associated with maintaining pregnant animals, however, it is expected that breath samples will be taken using this method earlier than is currently achievable, and may be done on more than one occasion to monitor pregnancy progress, depending on the primary producer's operational requirements. As noted above, the information regarding the animal's pregnancy state is key for making better business decisions on farm and better reproductive management is known to result in improved economic outcomes.

In other aspects, the present invention provides a method for determining a pregnancy state of an animal. In once of such aspects, the method comprises detecting an amount of one or more biomarkers indicative of a pregnancy state of the animal in a breath sample from the animal, and analysing the detected amount of the one or more biomarkers to determine the pregnancy state of the animal. In another of such aspects, the method comprises detecting an amount of one or more biomarkers indicative of a pregnancy state of the animal in a breath sample from the animal, and comparing the detected amount of the one or more biomarkers to a predetermined biomarker profile to determine the pregnancy state of the animal.

The steps in the methods of these aspects of the present invention may, for example, be as described herein in the context of the first aspect of the present invention.

The present invention also provides a sensor for detecting an amount of one or more biomarkers indicative of a pregnancy state of an animal in a breath sample from the animal, and then analysing the detected amount of the one or more biomarkers to determine the pregnancy state of the animal. The sensor may, for example, comprise a plurality or array of sensors that are configured to detect the biomarkers, whereby a (predetermined) cumulative response of the plurality of sensors is indicative of the animal being pregnant.

For example, the "Electronic Nose" sensor, sold under the brand Cyranose® by Sensigent, Los Angeles, USA, is a handheld chemical vapour sensing instrument designed to detect and identify complex chemical mixtures that constitute aromas, odours, fragrances, etc. The Cyranose® sensors have been used in industries including petrochemical, chemical, food and beverage, packaging materials, plastics, pet food, pulp and paper and medical research. The Cyranose® sensors utilise an array of detectors that are sensitive to chemical species incident upon them as well as advanced pattern recognition algorithms to detect and recognize the chemical vapour of interest via its "Smellprint". In combination, these technologies enable rapid detection and identification of substances based on their chemical profile, as visualized by the smellprint.

As will be described below, the inventor has demonstrated that a Cyranose® sensor was able to be adapted to detect the biomarkers described herein in a breath sample from the animal and to determine the pregnancy state of the animal. So-called "Electronic Nose" sensors should therefore be able to be provided which are suitable for use in the field and for detecting any particular combinations of biomarkers which are determined in accordance with the present invention to be indicative of pregnancy for a particular animal.

Thus, a system capable of detecting pregnancy in animals (such as cows, pigs and sheep) might be provided through the use of a breathalyser-type device that captures a sample of breath from the animal using a sampling device specifically made for a non-expert user to capture a breath sample without causing distress to the animal. The breath sample is then analysed using a sensor capable of determining individual components or volatiles present in the breath sample and, should the correct mix of components that signify pregnancy in the animal be identified, a positive result is provided.

The inventor believes that their ongoing research, utilising proven laboratory based research grade analysis technology, will enable them to better understand the patterns in biomarkers over time. Their further work aims to correlate the results obtained with a portable, on-farm device that will provide timely measurements in the field. Based on the data obtained thus far, some of which is described below, and on previous research and experience, the inventor expects that pregnancy screening could occur at possibly 16 days (a significant reduction, compared to current testing) using the method of the present invention.

The inventor also expects that the results of an animal's pregnancy state, as determined in accordance with the present invention, can be utilised in other applications. For example, the sensor described herein may automatically communicate the results to farm management software. Such results could also be integrated into automated animal handling equipment, for example in drafting pregnant animals from non-pregnant animals.

EXAMPLES

The inventor has conducted "Proof of concept" studies, where samples of cows' breath were analysed to confirm that biomarkers related to cow pregnancy could be detected. The results of this study are described below.

Example 1—Obtaining Breath Samples

In a first series of studies, cow breath samples were collected into purpose designed plastic bag containers where a 85 μm Carboxen™/Polydimethylsiloxane Solid Phase Micro Extraction (SPME) fibre was inserted into each bag for 30 minutes to concentrate the volatiles present in the breath samples.

50 cows in total were selected for the initial study and two baseline samples were taken of these animals before being artificially inseminated at t=0 (day 0). A baseline measurement of breath samples was performed at this stage using GCMS and the Electronic Nose methods, as described in Examples 2 and 4, respectively. Subsequent measurements were performed at days 7, 14, 21, 30, 60 and 80 days.

Confirmation of the pregnancy state of the animals were performed by a trained veterinarian using the method of palpation. This can be a subjective method, but is the standard method of verification used by industry. The response generated by these tests is a binary Yes/No response for pregnancy. These results were used to guide the Chemometric analyses to be performed on the data in this study to determine whether the analytical responses showed any biomarkers specific to pregnancy state.

This initial study was designed to be a 'broad net' capture of information from two proposed analytical methodologies, namely Gas Chromatography-Mass Spectroscopy (GCMS) as the primary reference method, and a new and promising portable technology based on the principles of the Electronic Nose, EN (Cyranose, Sensigent, Los Angeles, USA).

Example 2—Gas Chromatography-Mass Spectroscopic Analyses

The Carboxen™ fibre of Example 1 was directly injected into a GCMS system (Perkin Elmer Model Claris 680 GC with SQ8C Mass Spectrometer). The resulting Total Ion Chromatograph (TIC) and its associated Mass Spectra (MS) were extracted and analysed for biomarkers related to the pregnancy status of selected animals.

Mass spectroscopic data was imported into The Unscrambler (version 10.5.1. CAMO Software, Norway) for Multivariate (Chemometric) Analysis. Chemometrics is an established field that looks for chemical patterns in complex data sets, with chromatographic and spectroscopic data being representative data types. The baseline total ion chromatograph (TIC) is shown in FIG. 1 for reference.

Figure 2:
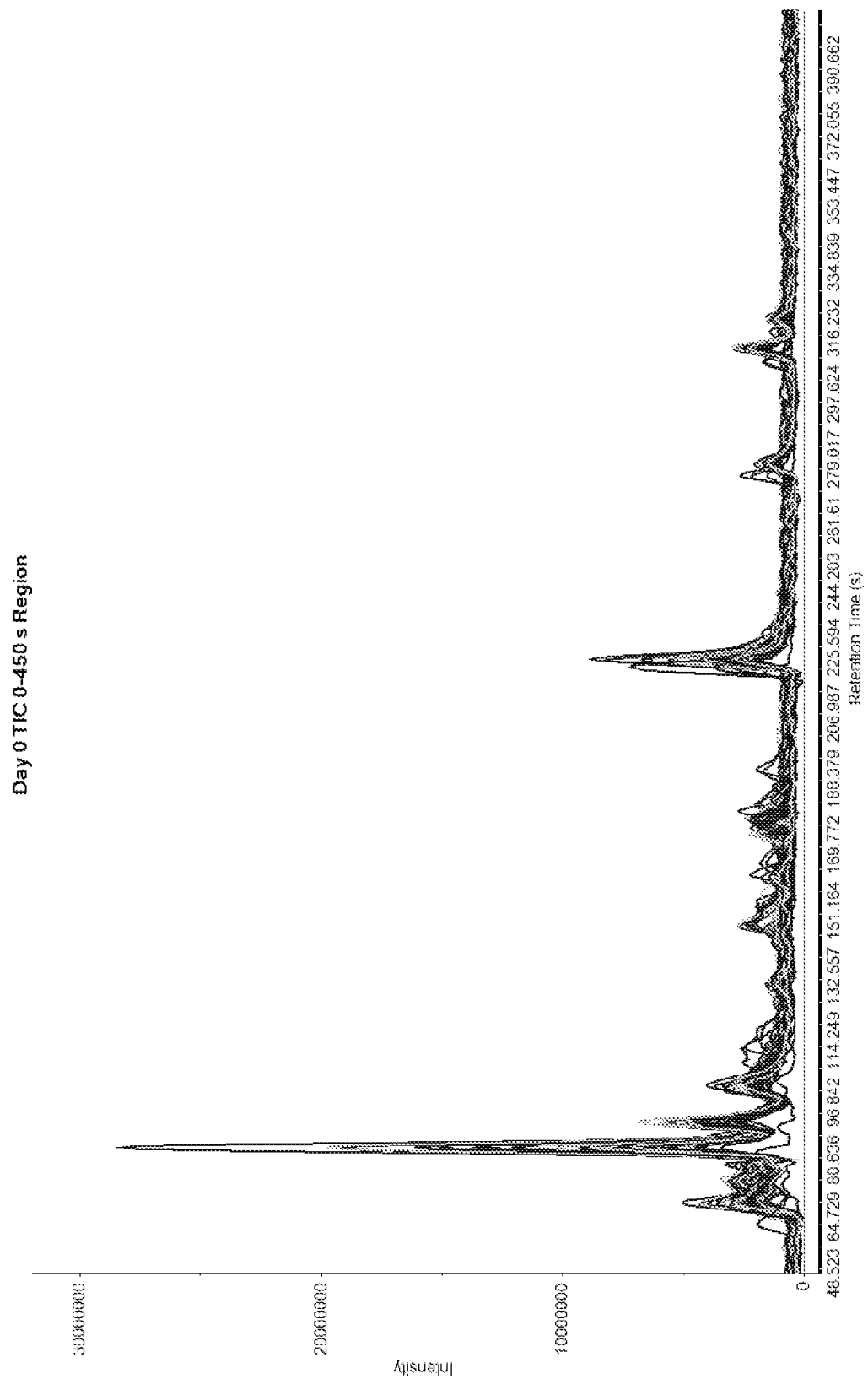
FIG. 2 is the TIC of FIG. 1, in the region 0 to 450 seconds.

The two predominant peaks in the TIC relate to N, N-Dimethylacetamide at 450 s and Phenol at 910 s from the Mass Spectra assignment against the NIST database. Below 450 s, a series of highly volatile compound peaks are observed and above 910 s a consistent and well resolved region can be observed. This initial investigation primarily focused on the region below 450 s. This region is shown in FIG. 2 and the TICs are colour coded by the pregnancy state of the cows. This data was smoothed to reduce the noise in the signal.

Figure 3:
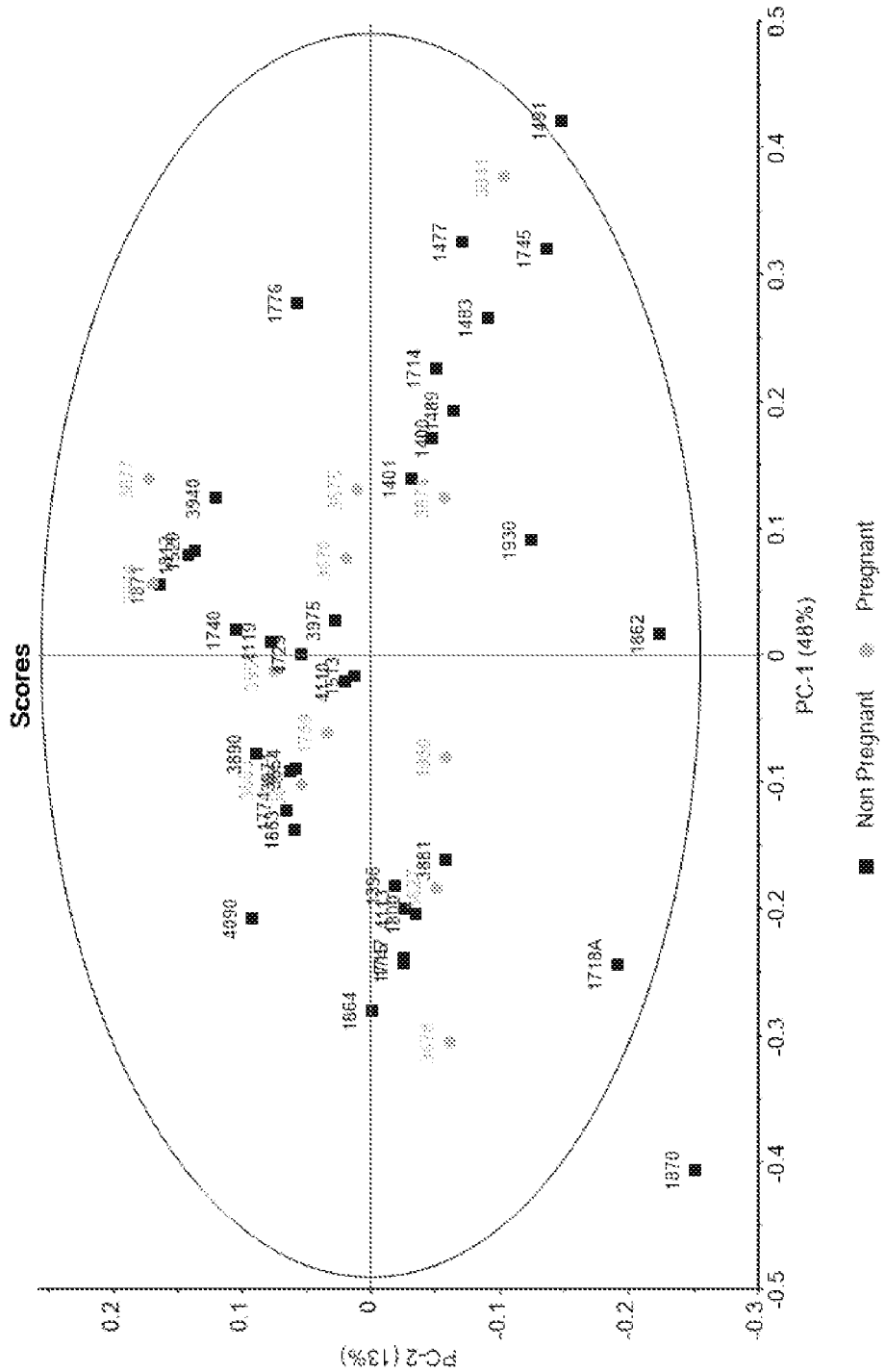
FIG. 3 depicts the Principal Component Analysis (PCA) Score plot of the baseline (Day 0) data for the TIC shown in FIG. 2.

The TICs in FIG. 2 show that there is no visible distinction between Pregnant and Non-Pregnant cows (as expected) and this was confirmed objectively using Principal Component Analysis (PCA). FIG. 3 shows the Scores plot of PCA, which is used to determine whether distinct classes can be observed in the data. In this case, the Non-Pregnant and Pregnant cows' results are interspersed with each other and shows that at time=0, all cows have an equivalent response to each other.

Figure 4:
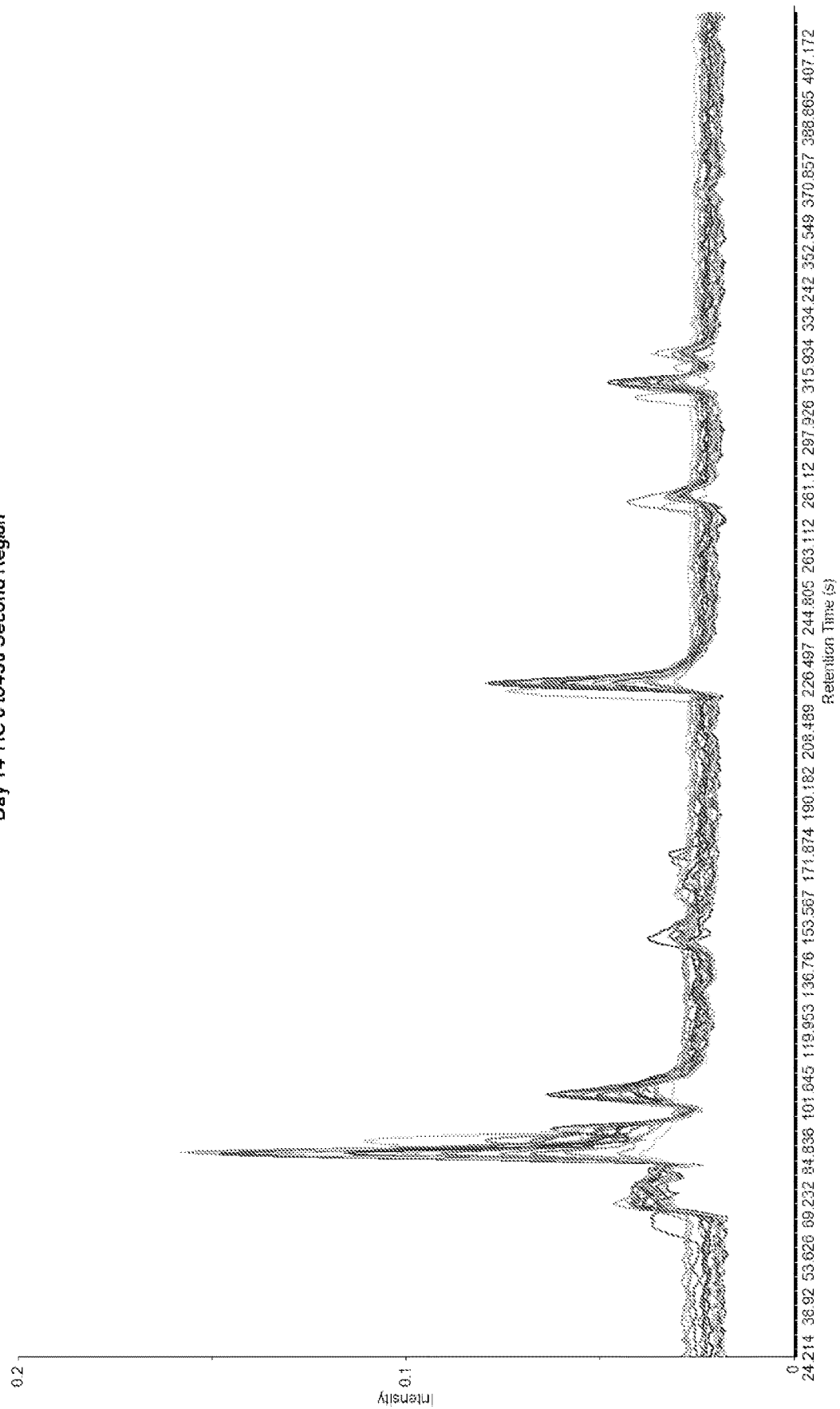
FIG. 4 is the 0 to 450 second region of the TIC for breath samples taken 14 days after insemination (note that the data has been smoothed and normalised)
Figure 5:
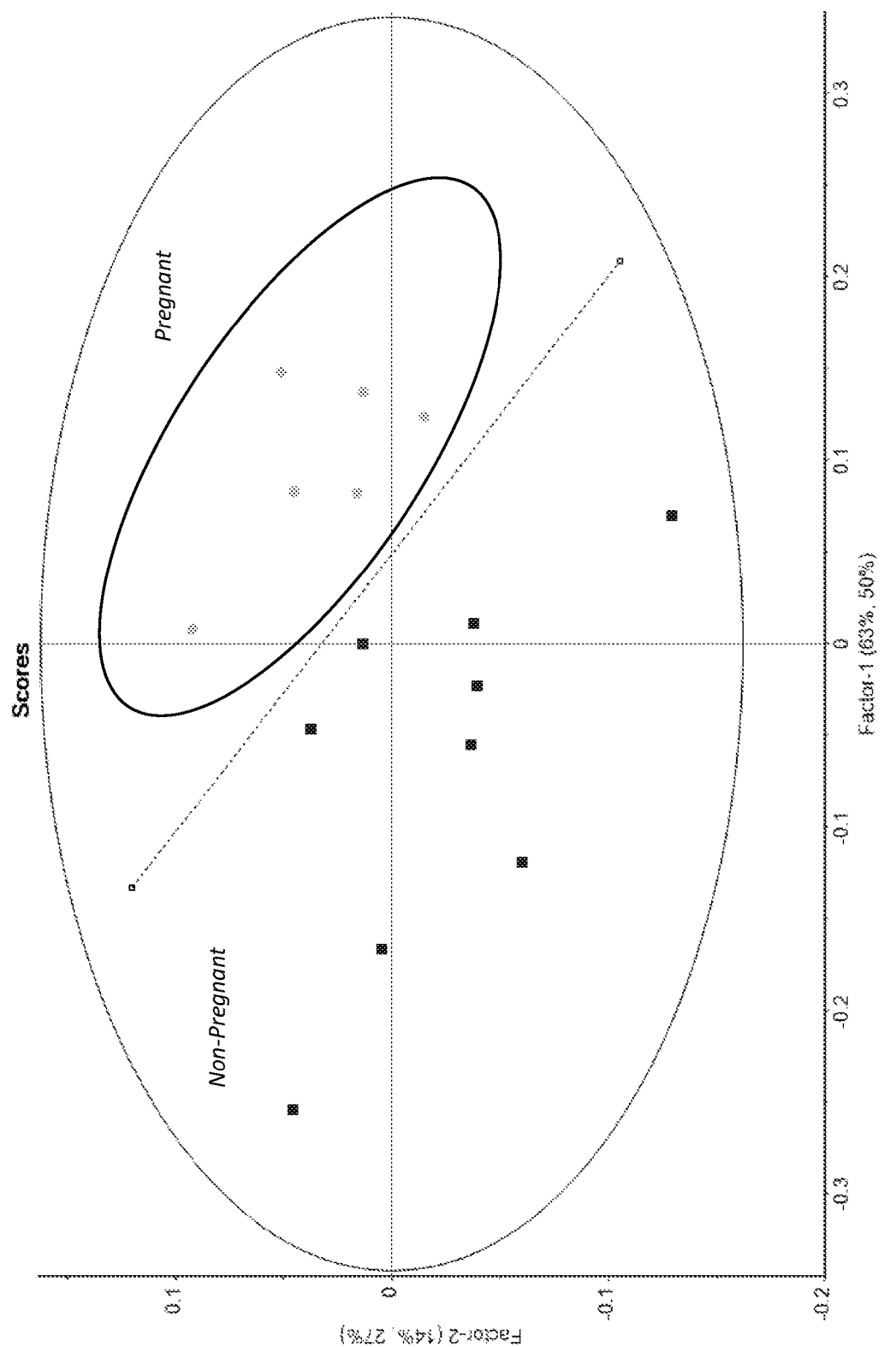
FIG. 5 shows the representation of the Partial Least Squares Discriminant Analysis (PLS-DA) Scores of Pregnancy obtained from the TIC shown in FIG. 4.

A portion of the day 14 samples were analysed on the main GCMS system, and the 0 to 450 second region of the TIC is shown in FIG. 4. The main method of data analysis used in this study is a method known as Partial Least Squares Discriminant Analysis (PLS-DA), which is a binary regression method that allows the prediction of class based on the chromatographic input data. The PLS-DA method is a powerful technique for such data sets and allows an assessment of the important variables contributing to the separation into pregnant and non-pregnant classes. In this case, these variables are the retention times of the compounds detected, which could then be further characterised by their Mass Spectra. In this case, the binary variable is Not-Pregnant vs. Pregnant. PLS-DA was applied to the Day 14 GCMS data and the Scores are shown in FIG. 5. FIG. 5 shows that at Day 14, biomarkers may be starting to be produced related to pregnancy. There were two outliers removed from this set and they appeared to have suspect baseline effects in the TIC.

Figure 6:
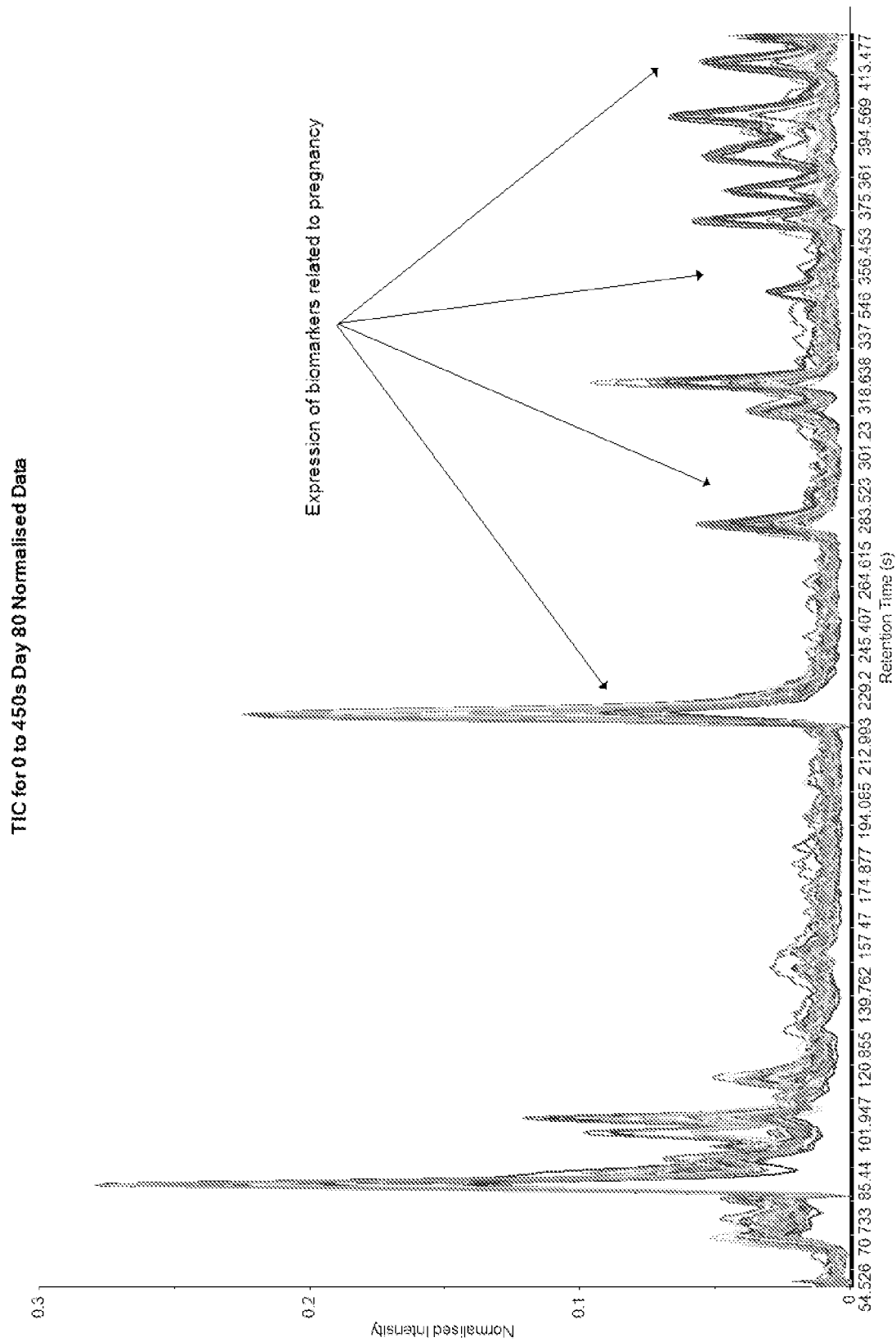
FIG. 6 is the 0 to 450 second region of the TIC for breath samples taken 80 days after insemination (note that the data has been smoothed and normalised)

Breath samples were also collected at day 80 in order to confirm that GCMS was in fact sensitive to pregnancy state. If so, then all of the confirmed non-pregnant cows should have a response similar to the day 0 baseline results. FIG. 6 shows the region of the TIC between 0-450 seconds for the day 80 data, and clearly indicate the presence of biomarkers related to pregnancy. These markers elute early in the chromatogram indicating their high volatility and are ideal for detection by the Electronic Nose method (described below).

Figure 7:
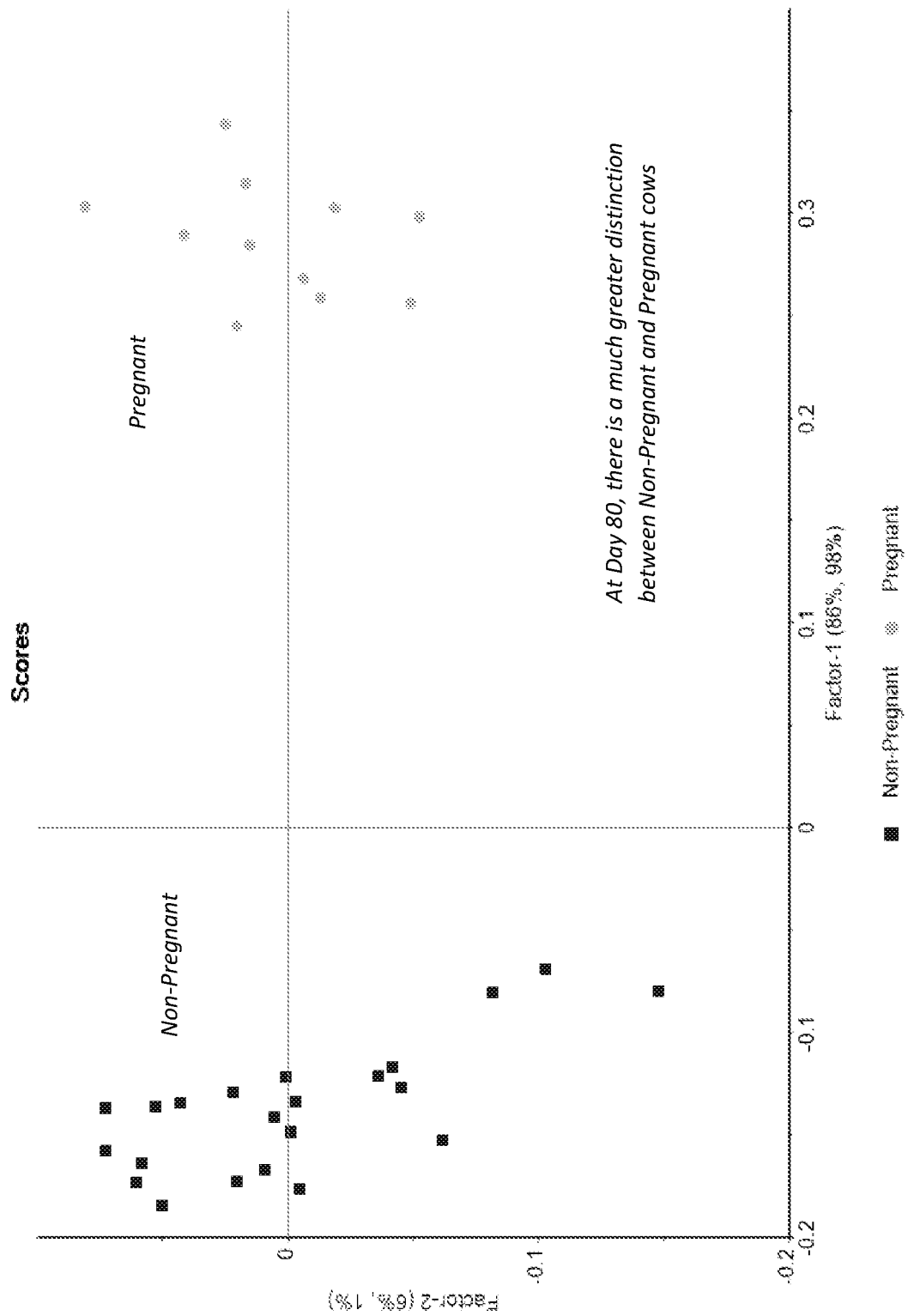
FIG. 7 shows the representation of the PLS-DA Scores of Pregnancy obtained from the TIC shown in FIG. 6.

To add objectivity to the analysis, the method of PLS-DA was applied to the data in FIG. 6. It was found that there were some shifts in the chromatograms (which were not corrected as part of this initial study) that caused some samples to be outliers. These could be removed with justification and attempts in the future will involve minimising such events from occurring. FIG. 7 shows the PLS-DA Scores plot for the day 80 data. Compared to the Scores plot in FIG. 5 for the Day 14 data, the day 80 data in FIG. 7 show much greater distinction between the non-pregnant and pregnant cows.

Figure 8:
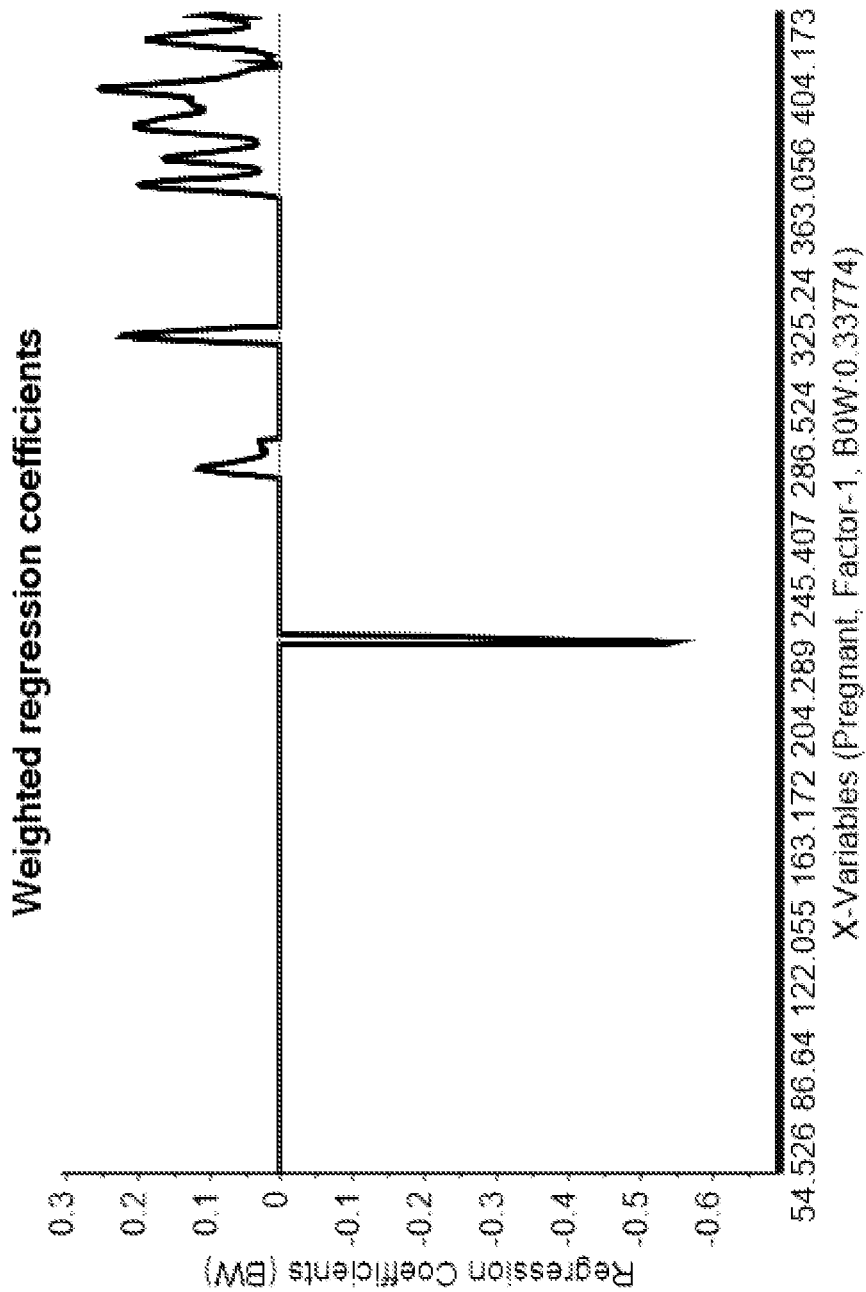
FIG. 8 shows the regression coefficients for the PLS-DA model of Non-Pregnant vs. Pregnant cows derived from the GCMS data.

FIG. 8 shows the Regression Coefficients, i.e. the important peaks at the retention times used to predict pregnancy from the TIC and the relationship between the compounds associated with pregnancy. In FIG. 8, the main observation is that as the peak at 229s decreases, the remaining biomarkers increase. Assignment of the nature of the biomarkers is ongoing, however, it is believed that these markers are related to one aromatic compound (toluene) at 229 second which decreases for pregnant cows, while the markers between 250 to 450 seconds are aliphatic compounds in the C6 to C9 mass range.

Figure 9:
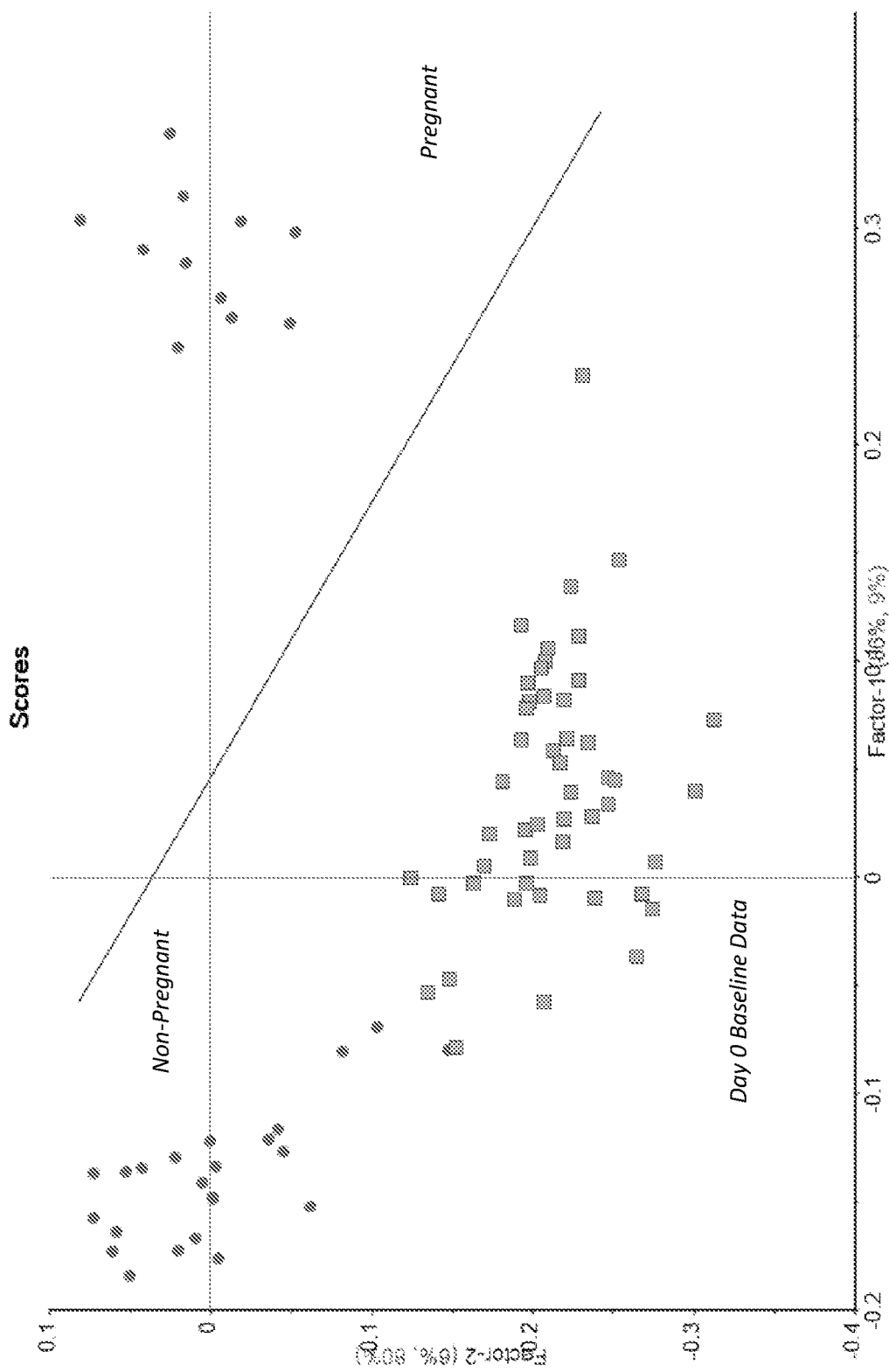
FIG. 9 shows the PLS-DA projection of Day 0 (baseline data) onto a pregnancy prediction model space.

The non-pregnant cow data was compared to the Day 0 baseline data. FIG. 9 shows that (within instrumental variation and for the purposes of this initial feasibility study) that the Day 0 data lie in a similar space to the non-pregnant cows at Day 80, and that the pregnant cows lie in their own space well separated from the non-pregnant and Day 0 data.

Based on this analysis, the GCMS techniques described above appear to be able to detect biomarkers in cow's breath related to pregnancy state. Pregnancy may potentially be detected from day 14, but more conclusively from day 80.

Example 3—Electronic Nose Analysis

Cow's breath samples present in the gaseous state and limit the application of commonly used handheld analytical technologies based on vibrational spectroscopic measurements, such as infrared spectroscopy, mainly due to sampling limitations. It was therefore decided to investigate the potential of "Electronic Nose" based technologies. These systems consist of an array of detectors (typically chemical specific polymers) that are sensitive to chemical species incident upon them. The exact nature of the sensors arrays specificity and selectivity is initially unknown and must be empirically determined based on an external method, GCMS in this case.

The initial study described in Example 2 investigated the sensitivity of a GCMS method for isolating specific biomarkers related to pregnancy state in cows and attempted to find the minimum time for detection of such biomarkers. A similar study on the Electronic Nose system was performed concurrently to determine whether it has the sensitivity to respond to the biomarkers produced by pregnant cows, as well as to establish the time point where the instrument was sensitive enough to detect such changes.

As described above, GCMS was able to detect the onset of pregnancy at day 14, but more conclusively at day 80. The Electronic Nose system described below was found to be sensitive to the biomarkers at day 60, although reproducibility has been found to be an issue for this specific configuration od sensors.

The Electronic Nose used in this study was a Cyranose® 320 (Sensigent), which uses an array of 31 sensors to detect chemical responses to the components of the cow's breath analysed. Data were collected for all days of the corresponding GCMS data measurements. The raw data presents in a manner that is not readily amenable to multivariate data analysis and therefore the final E-Nose profiles were manually calculated before the application of the PLS-DA algorithm.

Figure 10:
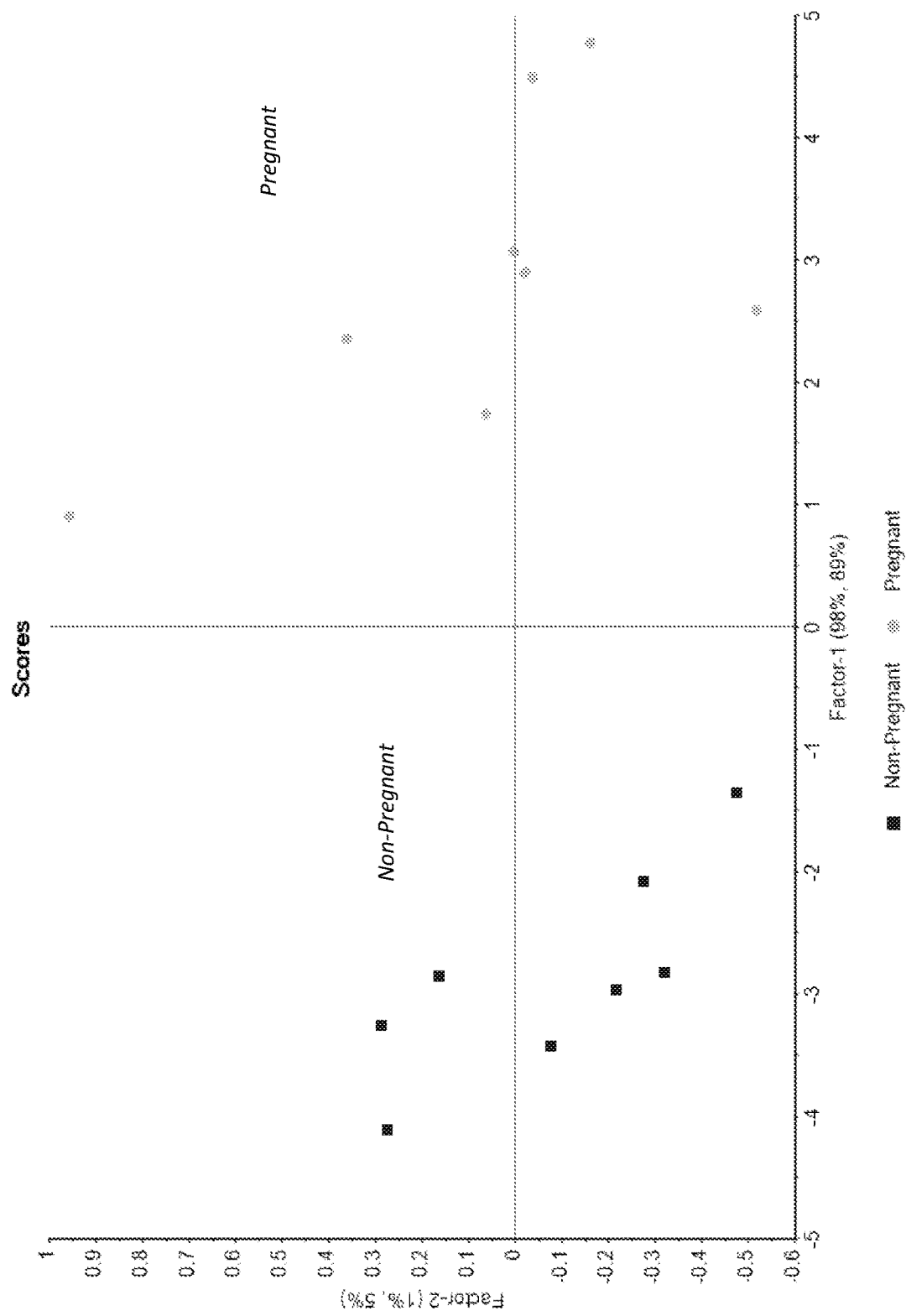
FIG. 10 shows the representation of the PLS-DA Scores of the Cyranose® sensor data for breath samples taken on day 60.

Cyranose data was collected on Day 60 and PLS-DA was performed on this data and there was a general pattern of non-pregnant and pregnant cow separations. There were however a few observations that did not fit the model. Based on the majority of the samples separating into non-pregnant and pregnant, these outliers were removed in this initial study and the Scores plot for the PLS-DA is shown in FIG. 10.

To further establish whether these were real signals from the Cyranose, the Day 30 Data were projected onto the Day 60 data, from which it could be seen that the Day 30 data lie in the same space as for non-pregnant cows.

Data were also collected using the Cyranose on Day 80. These data were projected onto the Day 60 Cyranose model and it was found that the results are consistent with the Day 60 results. This model can be used to predict the pregnancy state of the cows, albeit with some reproducibility issues, as described above.

In summary, Examples 1 to 3 describe an initial feasibility study to establish the utility of the present invention, namely that Gas Chromatography-Mass Spectrometry (GC-MS) can detect changes in biomarkers in cow's breath that can be used to assess the state of pregnancy of the cow, and that a portable, handheld point of use instrument, i.e. the Cyranose® Electronic Nose can be used to confirm pregnancy state.

The results from the GCMS and Cyranose trials, when compared to baseline measurements, showed that the differences between non-pregnant and pregnant cows are significantly different and therefore the conclusion drawn is that real information is being generated by the instruments that is consistent with the pregnancy state of the cows. This study has therefore confirmed the feasibility of both detection and analytical methods and leads to the general conclusion that the methods disclosed herein have a general applicability to the detection of the pregnancy state of an animal based on a breath sample. It is acknowledged that this study is preliminary in nature, but can be used as a basis for further work that will better optimise the methodology and also develop the sensor further to be more sensitive to the biomarkers found by GCMS.

Using the PLS DA algorithm, among other data analysis procedures, the primary analytical method of GCMS has been assessed using these algorithms in order to determine the pregnant/non-pregnant state of the animals under investigation. The multivariate methods used not only describe the important biomarkers present in the primary method data, but they also allow the modelling of such data with the secondary Electronic Nose data. In this manner, more justification for the secondary method can be established as it can be directly linked to the primary method of analysis. These methods can also be validated, making them more suitable for application filings, particularly with regulatory agencies.

Example 4

In a second series of studies, cow breath samples were collected into purpose designed plastic bag containers. The breath samples were extracted onto sorbent tubes within 4 hours of sampling and kept at 4° C. before analysis by quadrupole time of flight (qTOF) gas chromatography mass spectrometry at CSIRO's Mass spectrometric facility. For GC-MS analysis, volatiles extracted onto sorbent tubes were thermally desorbed using Unity 2 (Markes International) and transferred to a cold trap.

A gas chromatograph (Bruker 451 Model GC, Bruker Daltonik Inc., USA) using a GC capillary column ZB-5MS (Phenomenex Australia Pty Ltd.) 30 m in length, 0.25 mm ID, and 0.25 μm film thickness was used with the following temperature program: initial temperature 35° C. and held for 5 min, ramped to 180° C. at 5° C. min-1 then ramped to 250° C. at 8° C. min-1. The final temperature of 250° C. was held for 10 min. The total run time for the analysis was 53 min. Helium carrier gas flowed at a rate of 0.8 mL/min.

A single quadrupole mass detector (Scion SQ, Bruker Daltonik Inc., USA) set with a full scan detection covering the ion mass range from 35 to 350 m/z, with positive polarity.

Data was generated as raw .XMS files from Bruker. The files were converted into .CDF format using OpenChrom Edition software for statistical analysis.

Due to the complex nature of the GCMS data, multivariate data analysis (MVDA) methods were used to find patterns and trends in the data. The VEKTOR DIREKTOR™ software package from KAX Group was used for all data analyses performed. The methods used were Principal Component Analysis (PCA) and Partial Least Squares Discriminant Analysis (PLS-DA). Both methods used are commonly used in areas ranging from pharmaceutical manufacture, oil refining and agricultural applications using data collected from multichannel instruments. GCMS data were imported as CDF file formats. Initial array alignment was performed using the VEKTOR DIREKTOR array alignment tool. Due to the lower resolution of the instrumentation, further alignment of the data was performed using the correlation optimised warping (COW) method.

A number of cows were selected and two baseline samples were taken from these animals before being artificially inseminated at t=0 (day 0). A baseline measurement of breath samples was performed at this stage using GCMS, with subsequent measurements being performed at days 20, 40, 60 and 80.

Confirmation of the pregnancy state of the animals were performed by a trained veterinarian using the method of palpation. This can be a subjective method, but is the standard method of verification used by industry. The response generated by these tests is a binary Yes/No response for pregnancy. These results were used to guide the Chemometric analyses to be performed on the data in this study to determine whether the analytical responses showed any biomarkers specific to pregnancy state.

GCMS data were obtained from the breath samples described above obtained at baseline (i.e. the day of insemination) and at 20-day intervals up to day 80. An assessment of the chromatographic data initially performed and, based on the day 40 dataset, a promising model was developed that had the potential to separate pregnant and non-pregnant cows based on the data collected using the sampling device. This model was subsequently used to analyse the datasets from the other collections on days 20, 60 and 80.

Day 20

The mass spectra for breath samples taken on day 20 was obtained and, despite the environmental conditions on the day not being ideal, there are signs of the compounds observed at other collection days starting to appear in the M/Z region 240-270. A number of lower mass VOCs were also observed at 83, 115, 122, 125, 169 and 178. These may be related to hexanes and nonanes.

Figure 11:
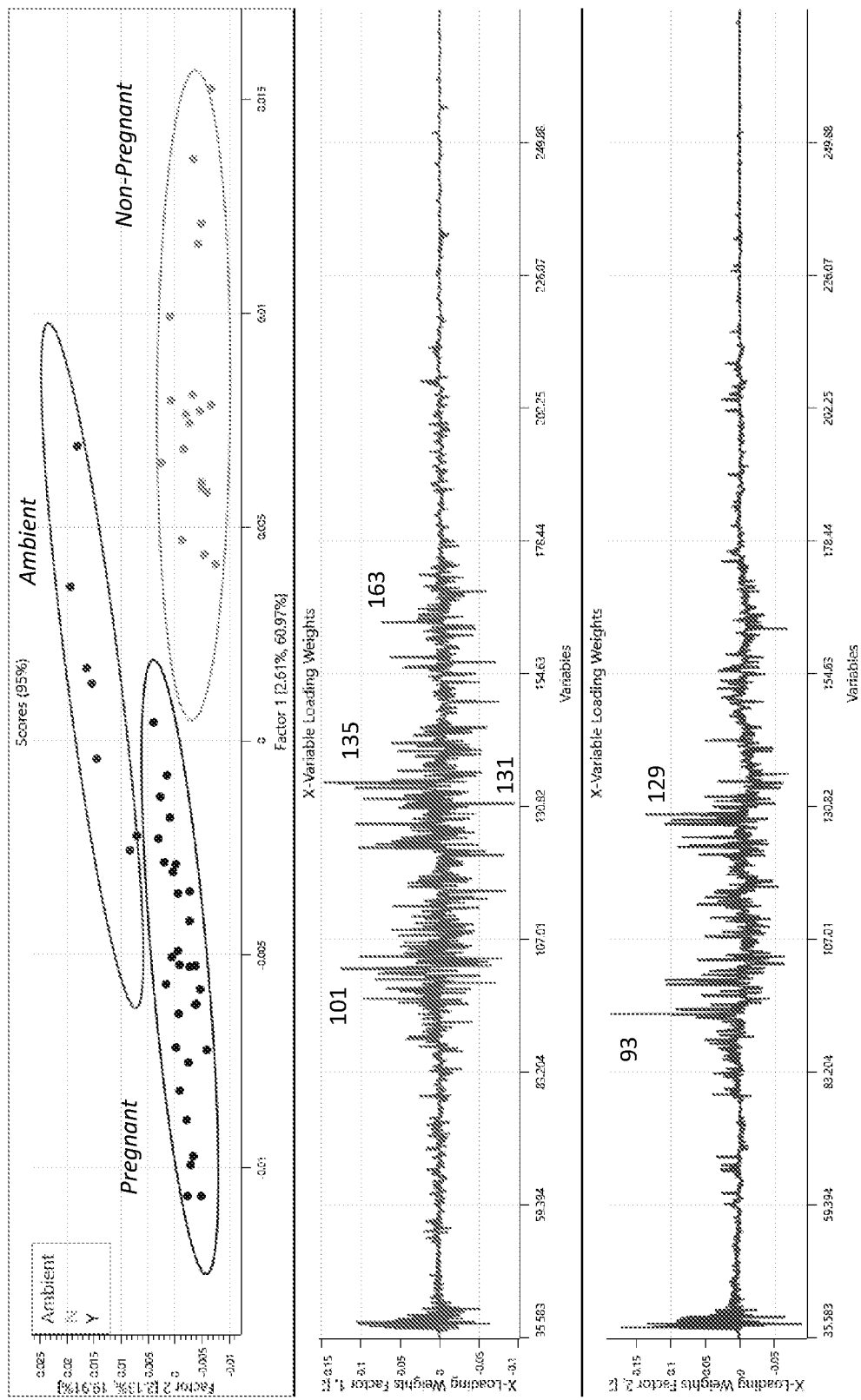
FIG. 11 shows the results of a PLS-DA applied to the dataset of the mass spectra of the breath samples collected from the cows at day 20.

FIG. 11 shows the results of a PLD-DA applied to this data. The PLS-DA scores show the characteristic pattern of factor 1 separating breath samples and factor 2 separating ambient air samples from breath samples. Although the peaks in the M/Z region 240-270 were observed, the lower mass VOCs seem to be dominating this analysis. At this stage, it is not known whether the environmental conditions of this data are not affecting the results.

Day 40

The mass spectra for day 40 data were collected on a GCMS using the same technique as for the day 20 samples. More defined peaks in the M/Z region between 240 and 270 were now observed, with the peaks at 243 and 262 related to non-pregnant cows. Table 1, set out below, shows the m/z of species identified on the mass spectra as being indicative of the pregnancy state of the cow.

TABLE 1 identification of peaks in the mass spectra which are biomarkers indicative of the animal's pregnancy state.

| Variable (m/z) | p value | LOG(p value) | Effect |
| --- | --- | --- | --- |
| 246.7 | 0.007 | 2.14 | down |
| 246.8116 | 0.008 | 2.10 | down |
| 215.0932 | 0.012 | 1.91 | up |
| 194.7108 | 0.015 | 1.84 | down |
| 204.8183 | 0.015 | 1.82 | down |
| 77.3305 | 0.018 | 1.74 | up |
| 198.1731 | 0.019 | 1.72 | up |
| 124.0704 | 0.020 | 1.70 | up |
| 46.89649 | 0.024 | 1.63 | up |
| 150.2046 | 0.024 | 1.62 | down |
| 230.394 | 0.025 | 1.61 | up |
| 177.7906 | 0.026 | 1.58 | down |
| 39.80453 | 0.028 | 1.56 | down |
| 188.3448 | 0.030 | 1.52 | down |
| 185.441 | 0.031 | 1.50 | down |
| 187.8981 | 0.032 | 1.49 | up |
| 72.08133 | 0.033 | 1.48 | up |
| 188.2331 | 0.035 | 1.46 | down |
| 205.7676 | 0.036 | 1.45 | up |
| 135.3506 | 0.037 | 1.44 | down |
| 124.3496 | 0.037 | 1.43 | up |
| 82.18877 | 0.041 | 1.39 | up |
| 200.4626 | 0.041 | 1.38 | up |
| 240.8365 | 0.042 | 1.37 | down |
| 101.8452 | 0.043 | 1.37 | up |

TABLE 1-continued identification of peaks in the mass spectra which are biomarkers indicative of the animal's pregnancy state.

| Variable (m/z) | p value | LOG(p value) | Effect |
| --- | --- | --- | --- |
| 156.0122 | 0.043 | 1.37 | down |
| 101.7336 | 0.043 | 1.37 | up |
| 107.597 | 0.044 | 1.36 | up |
| 156.8498 | 0.045 | 1.35 | down |
| 114.3539 | 0.045 | 1.34 | up |
| 42.76417 | 0.046 | 1.34 | up |
| 36.73321 | 0.050 | 1.30 | up |

Figure 12:
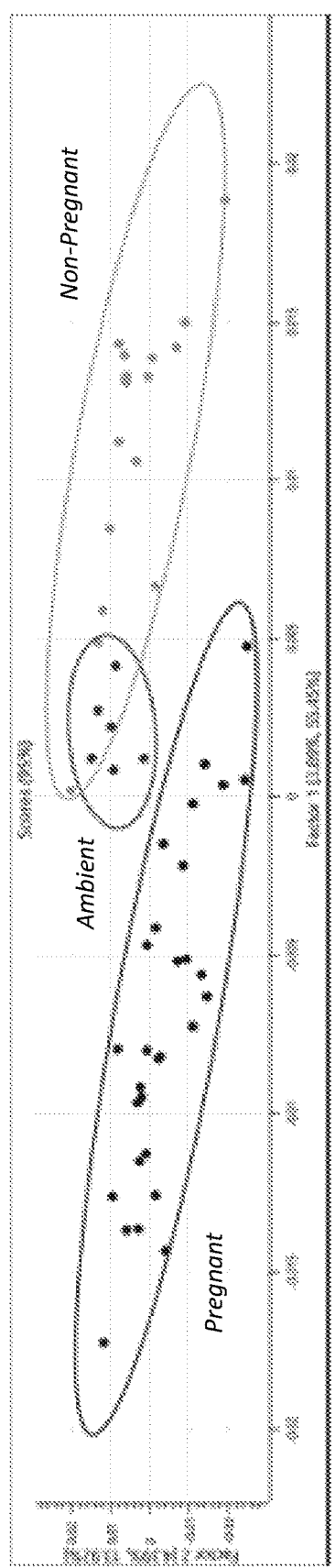
FIG. 12 shows the results of a PLS-DA applied to the dataset of the mass spectra of the breath samples collected from cows at day 40.

The mass spectra show a number of regions where pregnant and non-pregnant cows have particular VOCs related to them and the PLS-DA results are provided in FIG. 12. As was the case with day 20, the majority of the separation of the data is occurring in the M/Z region between 100 and 160. This may be indicative of various stages during pregnancy and a change in the VOCs during the various stages.

The PLS-DA scores plot shows very little separation between non-pregnant and ambient air VOCs. This may be explained as the majority of the air being composed of breath from non-pregnant cows and highlights the importance of establishing good separation between breath and ambient air samples.

The following M/Z peaks were found to be important for separating pregnant and non-pregnant cows, 96, 102, 129, 134, 136. More detailed analyses of these peaks has been performed in order to establish if these are fragments of larger ions, or if these are the primary ions.

The pattern of separation in FIG. 12 is a little different in this data, however, there is still a clear separation of pregnant and non-pregnant cows.

Day 60

Figure 13:
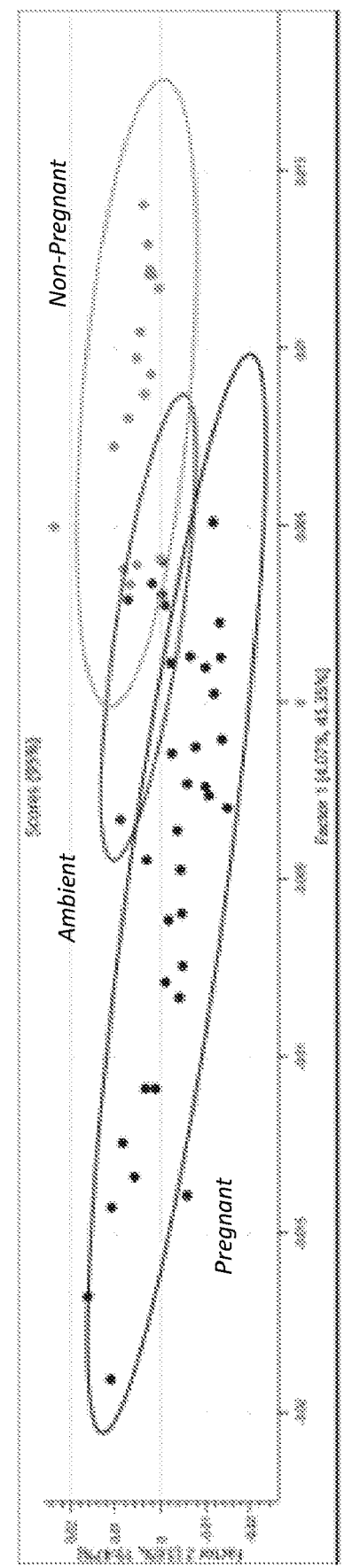
FIG. 13 shows the results of a PLS-DA applied to the dataset of the mass spectra of the breath samples collected from cows at day 60.

The mass spectra for day 60 data were collected on a GCMS using the same technique as for the day 20 and 40 samples and the PLS-DA assessment of this data is shown in FIG. 13.

The pattern of separation resembles the day 40 data, with clear separation of pregnant and non-pregnant cows. Ambient air appears to be an intermediate between pregnant and non-pregnant cow breath.

In the PLS-DA assessment in FIG. 13, separation of pregnant and non-pregnant cows and ambient air is along the factor 1 and factor 2 directions. This is indicating a mixing of sample types and may be is an indicator of pregnant and non-pregnant VOCs are present to a large degree in the ambient air samples. The M/Z region between 100 to 110 is showing the greatest separation between pregnant and non-pregnant breath samples and ambient air.

Day 80

Figure 14:
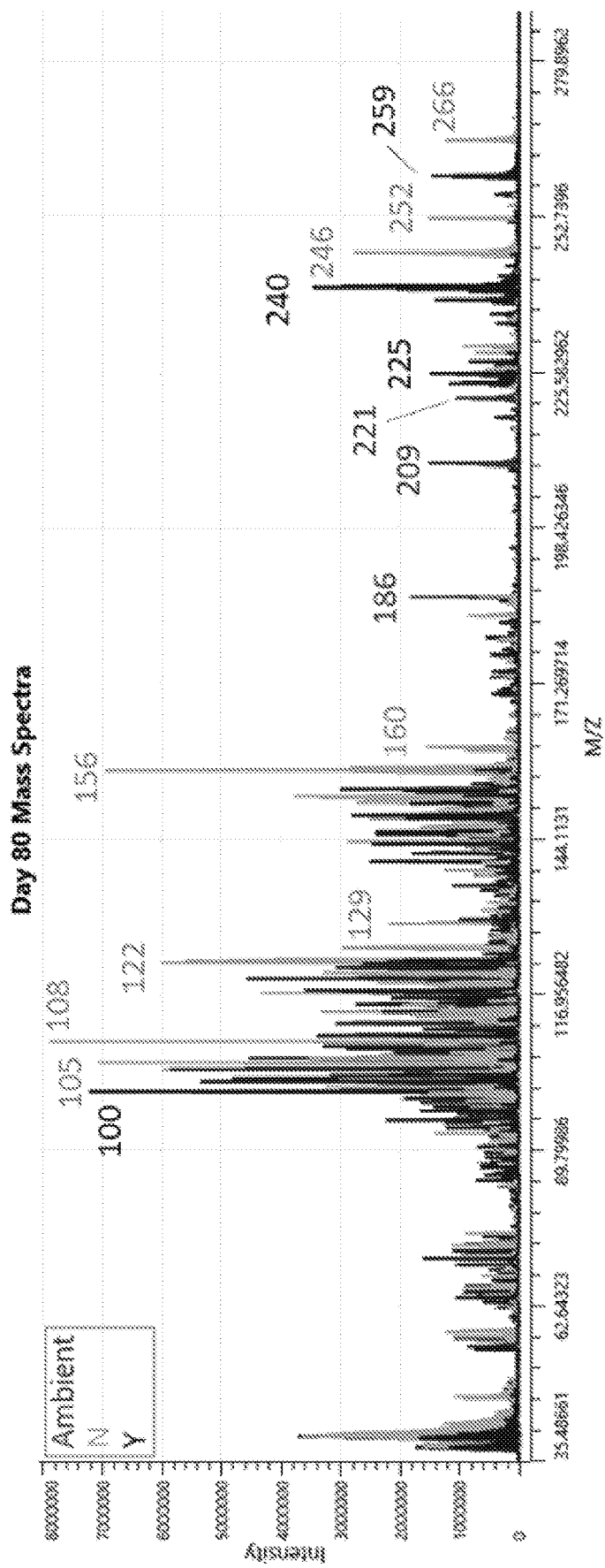
FIG. 14 shows the mass spectra of the breath samples collected from cows at day 80.

FIG. 14 shows the mass spectra for breath samples collected on day 80 grouped by pregnant, non-pregnant and ambient air. There are distinct mass values associated with pregnant, non-pregnant cows and ambient air samples.

Figure 15:
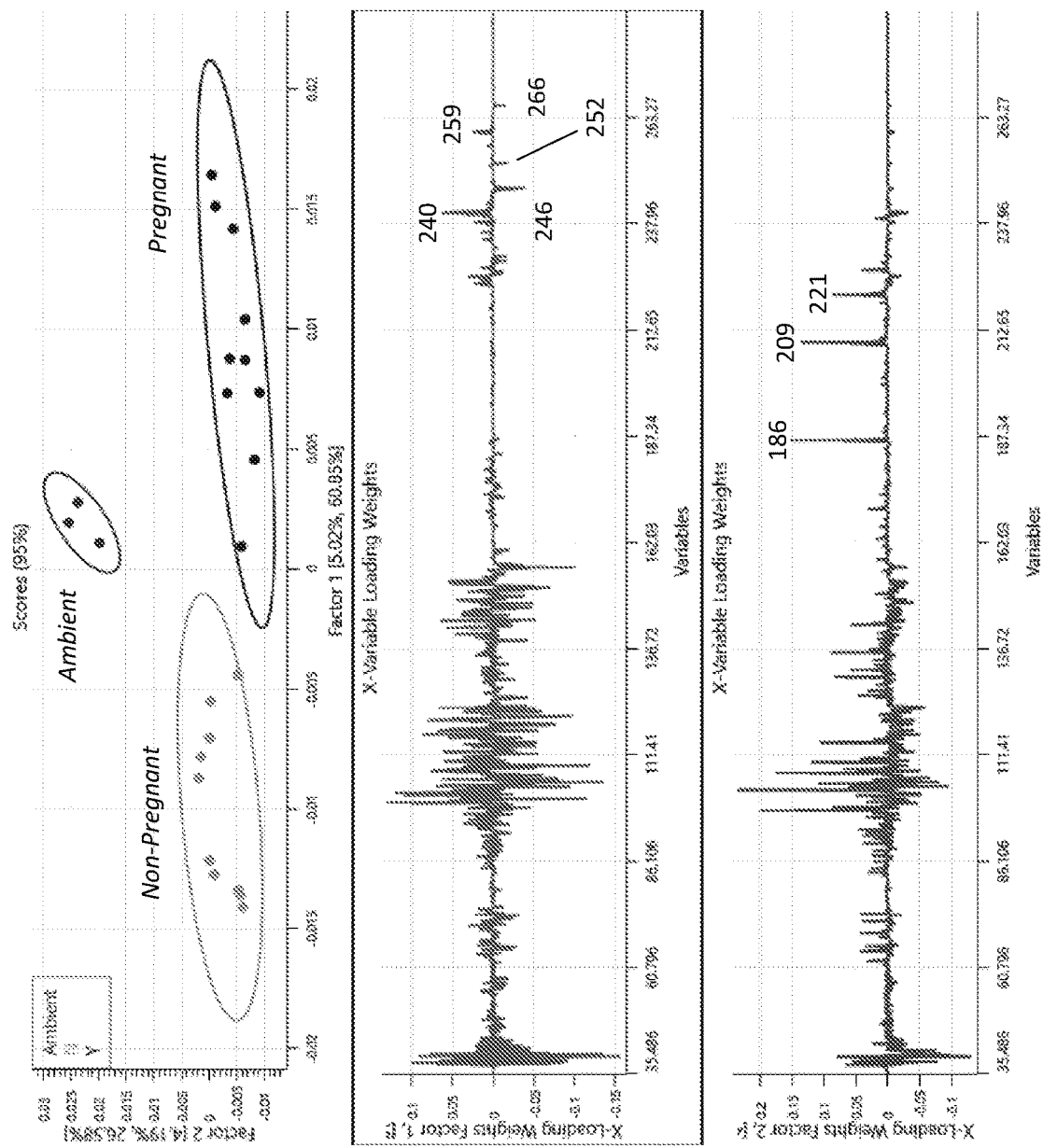
FIG. 15 shows the results of a PLS-DA applied to the dataset of the mass spectra of the breath samples collected from the cows at day 80.

There is a clear separation of VOCs related to pregnant and non-pregnant cows and also for ambient air. These data were assessed using multivariate analysis methods and the results. The results of a PLS-DA on normalised CSIRO GCMS data are shown in FIG. 15.

The PLS-DA scores plot shows that three distinct groups are visible for pregnant, non-pregnant and ambient air. The PLS-DA Factor 1 direction describes the differences between pregnant and non-pregnant cows and the Factor 2 direction describes the differences between ambient air and breath samples.

The loading weights for factor 1 shows high positive weighting at M/Z values of 259 and 240 consistent with the two values for pregnant cows observed in FIG. 14. Negative loading weights at 266, 256 and 246 indicate that the VOC(s) associated with these masses are associated with non-pregnant cows.

The loadings weights for factor 2 show positive weighting at M/Z values of 221, 209 and 186. These results show that these values represent the compound(s) present in ambient air.

Together, this analysis shows that the mass spectra can be used to separate pregnant and non-pregnant cows and also ambient air can be distinguished from breath samples.

The scores plot of FIG. 15 shows a distinct separation of pregnant, non-pregnant and ambient air samples. The factor 1 loading weight direction describes the VOC(s) associated with separating pregnant and non-pregnant cows and the factor 2 loading weight direction describes the difference between breath and ambient air samples. The M/Z values observed in the mass spectra are also observed in the loading weight plots.

Example 4 demonstrates that analysis of the mass spectra of cow's breath and ambient air samples is capable of separating between pregnant and non-pregnant cows and, in many cases, clear separation of ambient air from breath samples. This assessment shows a consistent pattern of separation using the PLS-DA method and serves as an indicator of VOC molecular masses of importance as biomarkers of pregnancy.

As described herein, the present invention provides methods for determining a pregnancy state of an animal from a breath sample. Embodiments of the present invention would provide a number of advantages over existing pregnancy detection methods, including:
short- and long-term business benefits, including:
Cost reduction in palpation testing per animal;
Reduction in costs related to maintenance of non-pregnant animals;
Introduction of precision farming aspects through better grazing programs;
Better management of pregnant animals compared to current practices;
The ability to better predict at an earlier stage birth dates and hence future sales;
the simplicity of a hand held system would reduce labour costs and make pregnancy testing a non-invasive process requiring little, if any, skill;
reduced carrying of empty cows would translate into better grazing management;
ability to sell empty cows earlier would increase income to farm;
non-invasive nature of pregnancy screening improves occupational health and safety on farm;
non-invasive nature of product enhances perception of farmers as acting with the health and wellbeing of animals in mind; and
provides an additional option for vets and reduces the time they have to undertake unpleasant and physically demanding/risky activities.

It will be understood to persons skilled in the art of the invention that many modifications may be made without departing from the spirit and scope of the invention. All such modifications are intended to fall within the scope of the following claims.

It is to be understood that any prior art publication referred to herein does not constitute an admission that the publication forms part of the common general knowledge in the art.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for determining whether an animal is pregnant, the method comprising:
collecting a breath sample from the nose of the animal;
detecting an amount of one or more biomarkers in the breath sample, wherein at least one of the one or more biomarkers is a metabolite of a metabolic process affected by the animal being pregnant; and
comparing the detected amounts of the one or more biomarkers with ambient air and a predetermined biomarker profile, the amount of each biomarker being indicative of the animal being pregnant;
wherein the one or more biomarkers are selected from one or more of the following:
toluene, hexanal, tridecane, tetradecane, propanoic acid, pentane, 1,3-epoxy-4-methyl, 3,5 dimethyl 2 octanone, 4-undecanone and 4-octanone.

2. The method of claim 1, wherein the predetermined biomarker profile comprises an accumulation of detected amounts of the one or more biomarkers in breath samples from animals of the same species having a categorised pregnancy state.

3. The method of claim 2, further comprising producing mass spectra for a plurality of points of the chromatographically resolved breath sample, whereby a mass spectral dataset is produced.

4. The method of claim 3, wherein the mass spectral dataset is analysed to determine whether the animal is pregnant.

5. The method of claim 4, wherein the analysis is a multivariate analysis.

6. The method of claim 3, wherein the analysis is a partial least squared discriminant analysis.

7. The method of claim 1, wherein detecting the amount of the one or more biomarkers comprises chromatographically resolving the breath sample.

8. The method of claim 1, wherein detecting an amount of the one or more biomarkers comprises contacting the breath sample with a plurality of sensors that are configured to sense the one or more biomarkers, whereby a cumulative response of the sensors is indicative of the animal being pregnant.

9. The method of claim 1, wherein at least one of the one or more biomarkers is a metabolite of a metabolic process affected by the pregnancy of a cow, sheep or pig.

* * * * *